United States Patent
Jarrard et al.

(10) Patent No.: US 11,721,021 B2
(45) Date of Patent: *Aug. 8, 2023

(54) IMAGE ANALYSIS OF EPITHELIAL COMPONENT OF HISTOLOGICALLY NORMAL PROSTATE BIOPSIES PREDICTS THE PRESENCE OF CANCER

(71) Applicants: Wisconsin Alumni Research Foundation, Madison, WI (US); The Medical College of Wisconsin, Inc., Milwaukee, WI (US)

(72) Inventors: David Frazier Jarrard, Madison, WI (US); Bing Yang, Madison, WI (US); Peter LaViolette, Milwaukee, WI (US)

(73) Assignees: Wisconsin Alumni Research Foundation, Madison, WI (US); The Medical College of Wisconsin, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/895,221

(22) Filed: Aug. 25, 2022

(65) Prior Publication Data

US 2022/0414878 A1    Dec. 29, 2022

Related U.S. Application Data

(63) Continuation of application No. 16/723,595, filed on Dec. 20, 2019, now Pat. No. 11,449,987.
(Continued)

(51) Int. Cl.
*G06T 7/00* (2017.01)
*G16H 30/40* (2018.01)
(Continued)

(52) U.S. Cl.
CPC ............ *G06T 7/0012* (2013.01); *G01N 1/30* (2013.01); *G16H 30/40* (2018.01); *G16H 50/30* (2018.01);
(Continued)

(58) Field of Classification Search
CPC ......... G06T 7/0012; G06T 2207/10056; G06T 2207/20081; G06T 2207/30024;
(Continued)

(56) References Cited

U.S. PATENT DOCUMENTS

| 6,677,157 B1 | 1/2004 | Cohen |
| 2006/0014238 A1 | 1/2006 | Gholap et al. |

(Continued)

FOREIGN PATENT DOCUMENTS

WO    WO 2015054666 A1    4/2015

OTHER PUBLICATIONS

Agnieszka et al. Aberrant epigenetic modifications in the CTCF binding domain of the IGF2/H19 gene in prostate cancer compared with benign prostate hyperplasia, (2009) International Journal of Oncology 35, 87-96.
(Continued)

*Primary Examiner* — Nay A Maung
*Assistant Examiner* — Jose M Torres
(74) *Attorney, Agent, or Firm* — Daniel A. Blasiole; DeWitt LLP

(57) ABSTRACT

A method of detecting the presence of a prostate cancer in a human subject comprising the steps of (a) obtaining a histologically normal prostate tissue sample from the patient and (b) quantifying the epithelial thickness or gland lumen roundness of the tissue, wherein an increase in epithelial
(Continued)

thickness or a decrease in gland lumen roundness indicates the presence of prostate cancer or a prostate cancer field defect.

15 Claims, 6 Drawing Sheets
(2 of 6 Drawing Sheet(s) Filed in Color)

Related U.S. Application Data

(60) Provisional application No. 62/783,879, filed on Dec. 21, 2018.

(51) Int. Cl.
  *G16H 50/30* (2018.01)
  *G01N 1/30* (2006.01)

(52) U.S. Cl.
  CPC .  *G01N 2001/302* (2013.01); *G01N 2001/305* (2013.01)

(58) Field of Classification Search
  CPC ............ G06T 2207/30081; G01N 1/30; G01N 2001/302; G01N 2001/305; G16H 30/20; G16H 30/40; G16H 50/20; G16H 50/30
  See application file for complete search history.

(56) References Cited

U.S. PATENT DOCUMENTS

| | | | |
|---|---|---|---|
| 2007/0104717 A1* | 5/2007 | Pienta .............. | G01N 33/57434 424/155.1 |
| 2009/0176218 A1 | 7/2009 | Cheng et al. | |
| 2012/0022793 A1 | 1/2012 | Barker et al. | |
| 2012/0135877 A1 | 5/2012 | Jarrard et al. | |
| 2012/0226709 A1 | 9/2012 | Bhargava et al. | |
| 2012/0290607 A1 | 11/2012 | Bhargava et al. | |
| 2013/0115604 A1 | 5/2013 | Watson et al. | |
| 2014/0286868 A1 | 9/2014 | Yates et al. | |
| 2014/0296355 A1 | 10/2014 | Jarrard et al. | |
| 2015/0268226 A1 | 9/2015 | Bhargava et al. | |
| 2017/0084021 A1 | 3/2017 | Athelogou et al. | |
| 2018/0135136 A1 | 5/2018 | Jarrard et al. | |
| 2018/0136215 A1 | 5/2018 | Jarrard et al. | |
| 2020/0077964 A1* | 3/2020 | Leroy .................. | G06T 11/001 |
| 2021/0122833 A1 | 4/2021 | Hu et al. | |

OTHER PUBLICATIONS

Aitchison A, et al. RASSF1A promoter methylation is frequently detected in both pre-malignant and non-malignant microdissected prostatic epithelial tissues. Prostate 2007;67(6):638-44 doi 10.1002/pros.20475.
Brooks, D. D., et al. "Prostate cancer screening 2010: updated recommendations from the American Cancer Society." Journal of the National Medical Association 102.5 (2010): 423-429.
Chandran, U. R., et al. "Differences in gene expression in prostate cancer, normal appearing prostate tissue adjacent to cancer and prostate tissue from cancer free organ donors." BMC cancer 5.1 (2005): 45.
Chen et al., "Epithelium percentage estimation facilitates epithelial quantitative protein measurement in tissue specimens", Clinical Protemics, BioMed Central, vol. 10, No. 1, 2013, pp. 1-10.
Chung LW. Implications of stromal-epithelial interaction in human prostate cancer growth, progression and differentiation. Semin Cancer Biol 1993;4(3):183-92.
Dakubo GD, et al. Clinical implications and utility of field cancerization. Cancer Cell Int 2007;7:2 doi 10.1186/1475-2867-7-2.
Damaschke NA, et al. Epigenetic susceptibility factors for prostate cancer with aging. Prostate 2013;73(16):1721-30 doi 10.1002/pros.22716.

Ebenezar et al., "Stokes shift spectroscopy pilot study for cancerous and normal prostate tissues", Appl Opt. Jun. 1, 2012;51(16):3642-9.
Esbona K, et al. COX-2 modulates mammary tumor progression in response to collagen density. Breast Cancer Res 2016;18(1):35 doi 10.1186/s13058-016-0695-3.
Fritz et al. Effect of clopidogrel added to aspirin in patients with atrial fibrillation, (2009) The New England Journal of Medicine 360.
Fu VX, et al. Aging and cancer-related loss of insulin-like growth factor 2 imprinting in the mouse and human prostate. Cancer Res 2008;68(16):6797-802 doi 10.1158/0008-5472.CAN-08-1714.
Gann, P. H., et al. "Risk factors for prostate cancer detection after a negative biopsy: a novel multivariable longitudinal approach." Journal of Clinical Oncology 28.10 (2010): 1714.
Gertych et al., "Machine learning approaches to analyze histological images of tissues from radical prostatectomies", Computerized Medical Imaging and Graphics 46 (2015), pp. 197-208.
Ghosh K, et al. Independent association of lobular involution and mammographic breast density with breast cancer risk. J Natl Cancer Inst 2010;102(22):1716-23 doi 10.1093/jnci/djq414.
Girasole CR, et al. Significance of atypical and suspicious small acinar proliferations, and high grade prostatic intraepithelial neoplasia on prostate biopsy: implications for cancer detection and biopsy strategy. J Urol 2006;175(3 Pt 1):929-33; discussion 33 doi 10.1016/S0022-5347(05)00338-1.
Gore JL, et al. Optimal combinations of systematic sextant and laterally directed biopsies for the detection of prostate cancer. J Urol 2001;165(5):1554-9.
Hanson JA, et al. Gene promoter methylation in prostate tumor-associated stromal cells. J Natl Cancer Inst 2006;98(4):255-61 doi 10.1093/jnci/djj051.
Hayward SW, et al. Stromal-epithelial interactions in the normal and neoplastic prostate. Br J Urol 1997;79 Suppl 2:18-26.
Henrique, R., et al. "Epigenetic heterogeneity of high-grade prostatic intraepithelial neoplasia: clues for clonal progression in prostate carcinogenesis." Molecular Cancer Research 4.1 (2006): 1-8.
Howlader N, et al. SEER Cancer Statistics Review, 1975-2014, based on Nov. 2016 SEER data submission. National Cancer Institute, Bethesda, MD; Apr. 2017.
Huang W, et al. A colorful future of quantitative pathology: validation of Vectra technology using chromogenic multiplexed immunohistochemistry and prostate tissue microarrays. Hum Pathol 2013;44(1):29-38 doi 10.1016/j.humpath.2012.05.009.
Iremashvili V, et al. Prostate sampling by 12-core biopsy: comparison of the biopsy results with tumor location in prostatectomy specimens. Urology 2012;79(1):37-42 doi 10.1016/j.urology.2011.09.011.
Jemal, A. "Cancer statistics, 2009." Ca Cancer J Clin 59 (2009): 225-249.
Kwak et al., "Multimodal microscopy for automated histologic analysis of prostate cancer", MioMed Central Cancer, vol. 11, No. 62 pp. 1-16, Year: 2011.
Lee MC, et al. Multifocal high grade prostatic intraepithelial neoplasia is a risk factor for subsequent prostate cancer. J Urol 2010;184(5):1958-62 doi 10.1016/j.juro.2010.06.137.
Madabhushi A, et al. Image analysis and machine learning in digital pathology: Challenges and opportunities. Med Image Anal 2016;33:170-5 doi 10.1016/j.media.2016.06.037.
McGarry SD, et al. Radio-pathomic Maps of Epithelium and Lumen Density Predict the Location of High-Grade Prostate Cancer. Int J Radiat Oncol Biol Phys. 2018;101:1179-87. Available online Apr. 24, 2018.
McNeal JE, et al. Zonal distribution of prostatic adenocarcinoma. Correlation with histologic pattern and direction of spread. Am J Surg Pathol 1988;12(12):897-906.
McNeal JE. Normal histology of the prostate. Am J Surg Pathol 1988;12(8):619-33.
Mehrotra J, et al. Quantitative, spatial resolution of the epigenetic field effect in prostate cancer. Prostate 2008;68(2):152-60 doi 10.1002/pros.20675.
Morrison et al., "The connective tissue framework in the normal prostate, B.P.H. and prostate cancer: analysis by scanning electron microscopy after cellular digestion", Urol Res (2000) 28:304-307.

(56) References Cited

OTHER PUBLICATIONS

Nonn, L et al., "Evidence for field cancerization of the prostate." The Prostate 69.13 (2009): 1470-1479.
Page DL, et al. Anatomic markers of human premalignancy and risk of breast cancer. Cancer 1990;66(6 Suppl):1326-35.
Paradowska, A, et al. "Aberrant epigenetic modifications in the CTCF binding domain of the IGF2/H19 gene in prostate cancer compared with benign prostate hyperplasia." International journal of oncology 35.1 (2009): 87-96.
Sandhu R, et al. Digital histologic analysis reveals morphometric patterns of age-related involution in breast epithelium and stroma. Hum Pathol 2016;48:60-8 doi 10.1016/j.humpath.2015.09.031.
Schröder, F. H., et al. "Screening and prostate-cancer mortality in a randomized European study." New England Journal of Medicine 360.13 (2009): 1320-1328.
Schulz, W. A., et al. "Epigenetic mechanisms in the biology of prostate cancer." Seminars in cancer biology. vol. 19. No. 3. Academic Press, 2009. 172-180.
Tambasco M, et al. Quantifying the architectural complexity of microscopic images of histology specimens. Micron 2009;40(4):486-94 doi 10.1016/j.micron.2008.12.004.
Tambasco M, et al. Relationship between tumor grade and computed architectural complexity in breast cancer specimens. Hum Pathol. 2008;39:740-6.
Thompson, I. M., et al. "Prevalence of prostate cancer among men with a pro state-specific antigen level= 4.0 ng per milliliter." New England Journal of Medicine 350.22 (2004): 2239-2246.
Truong M, et al. Using the epigenetic field defect to detect prostate cancer in biopsy negative patients. J Urol 2013;189(6):2335-41 doi 10.1016/j.juro.2012.11.074.
Veltri RW, et al. Stromal-epithelial measurements of prostate cancer in native Japanese and Japanese-American men. Prostate Cancer Prostatic Dis 2004;7(3):232-7 doi 10.1038/sj.pcan.4500738.
Yang B, et al. Methylation profiling defines an extensive field defect in histologically normal prostate tissues associated with prostate cancer. Neoplasia 2013;15(4):399-408.
Yang B, et al. Validation of an epigenetic field of susceptibility to detect significant prostate cancer from non-tumor biopsies. Clin Epigenetics. 2019;11:168.
Yu, Y. P., et al. "Gene expression alterations in prostate cancer predicting tumor aggression and preceding development of malignancy." Journal of clinical oncology 22.14 (2004): 2790-2799.
Zhou M. High-grade prostatic intraepithelial neoplasia, PIN-like carcinoma, ductal carcinoma, and intraductal carcinoma of the prostate. Mod Pathol Jan. 2018;31(S1):S71-9 doi 10.1038/modpathol.2017.138.

\* cited by examiner

IMAGE ANALYSIS OF EPITHELIAL COMPONENT OF HISTOLOGICALLY NORMAL PROSTATE BIOPSIES PREDICTS THE PRESENCE OF CANCER

CROSS-REFERENCE TO RELATED APPLICATION

This application is a continuation of U.S. application Ser No. 16/723,595, filed Dec. 20, 2019, which claims priority to U.S. Provisional Application No. 62/783,879, filed Dec. 21, 2018, all of which are incorporated herein in their entireties.

STATEMENT REGARDING FEDERALLY SPONSORED RESEARCH OR DEVELOPMENT

Not applicable.

BACKGROUND

It is estimated that 198,280 men were diagnosed with prostate cancer and 27,360 men died from prostate cancer (PCa) in 2009 in the USA (Jemal et al., (2009) *CA Cancer J Clin* 59, 225-249). The predominant tools for early detection of prostate cancer are prostate specific antigen (PSA) testing and digital rectal exam (DRE). However, 65% to 70% of men with total PSA ranging between 4.0-10.0 ng/ml have a negative prostate biopsy result. In addition, 15% of PCa patients have PSA levels<4.0 ng/ml, indicating a weak predictive ability (Thompson et al., (2004) *N Engl J Med* 350, 2239-2246). PSA-based screening also detects non-significant cancers leading to an estimated 50% of overdiagnosis (Fritz et al., (2009) *The New England Journal of Medicine* 360). A urine-based test examining an RNA molecule termed PCA-3 is currently undergoing FDA trials. Prostate biopsy is used to confirm disease. However, because of sampling errors repeated sets of samples are commonly required to make a diagnosis (Gann et al., (2010) *JCO* 28, 7). Typical biopsy schemes include 10-12 or more tissue cores removed under local anesthetic. Re-biopsy is often required two to three times in order to rule out cancer because of sampling errors. Cancers can also be missed because of sampling problems.

There is a clear need for methods that allow easier and more accurate diagnosis and prognosis of prostate cancer.

SUMMARY OF THE INVENTION

In a first aspect, provided herein is a method of treating prostate cancer in a human subject comprising the steps of: (a) obtaining histologically normal prostate tissue from the subject; (b) quantifying epithelial thickness in the tissue; and (c) treating the human subject for prostate cancer when the epithelial thickness is increased by at least about 6% relative to the epithelial thickness measured in a sample from a healthy, tumor-free subject.

In a second aspect, provided herein is a method of treating prostate cancer in a human subject comprising the steps of: (a) obtaining histologically normal prostate tissue from the subject; (b) staining the tissue; (c) imaging the tissue; (d) quantifying epithelial thickness in the tissue; and (e) treating the human subject for prostate cancer when the epithelial thickness is increased by at least about 6% relative to the epithelial thickness measured in a sample from a healthy, tumor-free subject. In some embodiments, the tissue is stained with a stain specific for epithelial cells. In some embodiments, the stain is hematoxylin and eosin stain. In some embodiments, the stain is a high molecular weight cytokeratin stain.

In some embodiments, the tissue is imaged using an automated imaging system.

In some embodiments, the tissue is imaged and digitized using a microscope equipped with a camera or a digital microscope system. In some embodiments, the automated imaging system is selected from the group consisting of VECTRA™, Aperio eSlide Manager, TissueFAXS 220, TissueFAXS CONFOCAL PLUS 200, and a Huron™ slide scanner. In some embodiments, the epithelial thickness is measured using image analysis software. In some embodiments, the image analysis software is inForm2.1.1. In some embodiments, the epithelial thickness is increased by at least about 7%. In some embodiments, the epithelial thickness is increased by at least about 8%.

In a third aspect, provided herein is a method of treating prostate cancer in a human subject comprising the steps of: (a) obtaining histologically normal prostate tissue from the subject; (b) quantifying gland lumen roundness in the tissue; and (c) treating the human subject for prostate cancer when the gland lumen roundness is decreased by at least about 10% relative to the gland lumen roundness measured in a sample from a healthy, prostate tumor-free subject.

In a fourth aspect, provided herein is a method of treating prostate cancer in a human subject comprising the steps of: (a) obtaining histologically normal prostate tissue from the subject; (b) staining the tissue; (c) imaging the tissue; (d) quantifying gland lumen roundness in the tissue; and (e) treating the human subject for prostate cancer when the gland lumen roundness is decreased by at least about 10% relative to the gland lumen roundness measured in a sample from a healthy, prostate tumor-free subject. In some embodiments, the tissue is stained with a stain specific for epithelial cells. In some embodiments, the stain is hematoxylin and eosin stain. In some embodiments, the stain is a high molecular weight cytokeratin stain.

In some embodiments, the tissue is imaged using an automated imaging system.

In some embodiments, the tissue is imaged and digitized using a microscope equipped with a camera or a digital microscope system. In some embodiments, the automated imaging system is selected from the group consisting of VECTRA™, Aperio eSlide Manager, TissueFAXS 220, TissueFAXS CONFOCAL PLUS 200, and a Huron™ slide scanner. In some embodiments, the gland lumen roundness is measured using image analysis software. In some embodiments, the image analysis software is inForm2.1.1. In some embodiments, the gland lumen roundness is decreased by at least about 12%. In some embodiments, the gland lumen roundness is decreased by at least about 13%.

In a fifth aspect, provided herein is a method of measuring epithelium thickness in a human subject suspected of having prostate cancer comprising the steps of: (a) obtaining histologically normal prostate tissue from the subject; and (b) measuring epithelium thickness in the histologically normal prostate tissue. In some embodiments, the histologically normal prostate tissue is stained with a stain specific for epithelial cells prior to measuring epithelium thickness. In some embodiments, the stain is hematoxylin and eosin stain. In some embodiments, the stain is a high molecular weight cytokeratin stain.

In a sixth aspect, provided herein is, a method of measuring gland lumen roundness in a human subject suspected of having prostate cancer comprising the steps of: (a) obtaining histologically normal prostate tissue from the subject; and (b) measuring gland lumen roundness in the histologically normal prostate tissue. In some embodiments, the histologically normal prostate tissue is stained with a stain specific for epithelial cells prior to measuring gland lumen roundness. In some embodiments, the stain is hematoxylin and eosin stain. In some embodiments, the stain is a high molecular weight cytokeratin stain.

BRIEF DESCRIPTION OF DRAWINGS

This patent application file contains at least one drawing executed in color. Copies of this patent or patent application publication with color drawings will be provided by the Office upon request and payment of the necessary fee.

The invention will be better understood and features, aspects and advantages other than those set forth above will become apparent when consideration is given to the following detailed description thereof. Such detailed description makes reference to the following drawings, wherein:

(FIG. 1A) Demonstration of tissue segmentation analysis in a representative NTA core. Algorithms for tissue segmentation, i.e., epithelial versus stromal, were created by machine learning and epithelial, stromal and total area calculated for each biopsy. Lumen area was subtracted to generate epithelial area. Sample image of TA biopsy stained with hematoxylin (purple) and eosin (pink)×20 objective with tissue segmentation map after training the software. Red epithelial, green stromal, blue empty space. (FIG. 1B) The epithelial to total biopsy area for tumor associated (TA) (n=83) compared to non-tumor associated (NTA) (n=89) samples (p=0.0006). (FIG. 1C) Epithelial to stromal ratio for TA compared to NTA was significantly greater (p=0.002). (FIG. 1D) Biopsies stratified by location either apex, mid or base. Epithelial to total ratio for TA compared to NTA from mid prostate was significantly greater (p=0.02). Tumor associated (TA), non-tumor associated (NTA), ns not significant, *p<0.05, p<0.01, * p<0.001.

(FIG. 1A) Quantitation of epithelial to total area for TA (n=92) compared to NTA (n=87) was significantly greater (p=0.004). (FIG. 1B) Epithelial to stromal ratio for TA compared to NTA (p=0.004). (FIG. 1C) Staining of cytokeratin for epithelial quantitation was performed as described. Mean±SE pan-CK positive cells for TA (n=30) 18.1±1.7% compared to NTA (n=30) 17.4±1.6% was not significantly greater (p=0.75). (FIG. 1D) Comparison of epithelial to total area with patient age using cystoprostatectomy specimens (n=37) obtained from patients 28-86 years old demonstrated Pearson correlation coefficient of −0.03 (p=0.87). Tumor associated (TA), non-tumor associated (NTA), ns not significant, * p<0.05,  p<0.01, * p<0.001.

(FIG. 3A) Demonstration of the epithelial wall thickness calculation. The distance between each point along the individual lumen and the nearest glandular border were calculated (dotted lines). The average of these values was calculated and assigned to the individual lumen along with the gland volume, lumen volume, and gland lumen roundness. (FIG. 3B) Mean±SE epithelial thickness for TA (n=62) 3.11±0.12×10$^{-5}$ m and NTA (n=50) 2.88±0.12×10$^{-5}$ m was significantly different (p=0.006). (FIG. 3C) Mean±SE gland lumen roundness for TA 0.34±0.01 and NTA 0.38±0.02 was significantly different (p=0.001). (FIG. 3D) Mean±SE gland area for TA 6, 224.6±207.2 pixels and NTA 5, 734.3±215.2 pixels was not significantly different (p=0.10). (FIG. 3E) Mean±SE outer gland roundness for TA 0.25±0.008 and NTA 0.24±0.008 was not significantly different (p=0.70). (FIG. 3F) Mean±SE epithelial nuclear density for TA 0.18±0.008 cells/10$^{-5}$ m$^2$ and NTA 0.18±0.01 cells/10$^{-5}$ m$^2$ was not significantly different (p=0.51). Tumor associated (TA), non-tumor associated (NTA), *p<0.05, **p<0.01.

FIG. 4 is a flowchart illustrating the steps of an example method for inputting image data depicting a tissue sample to generate output as feature data indicative of epithelial content, stromal content, tissue content, or combinations thereof, which may include measurements, estimates, or predictions of epithelial thickness, gland lumen roundness, or so on.

DESCRIPTION OF THE PRESENT INVENTION

In General

Figures 1A, 1B, 1C, 1D:
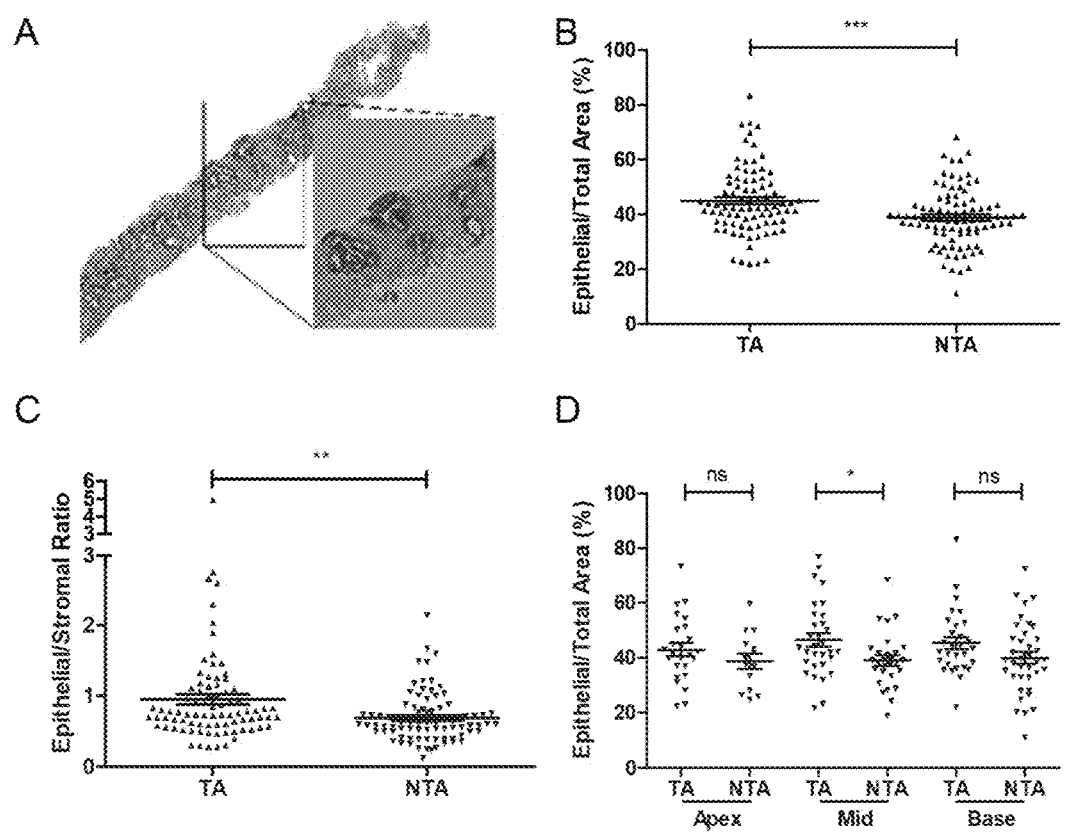
FIGS. 1A-1D show quantitative histologic data of training set (n=172) obtained with InForm2.1.1 software (Perkin Elmer) using H&E stained cancer negative prostate biopsy cores.

Like other human cancers, prostate cancer development and progression is driven by the interplay of genetic and epigenetic changes (Schulz et al., (2009) *Semin Cancer Biol* 19, 172-180). Genetic and epigenetic alterations do not appear to be limited to the cancerous cells, as recent data indicates tissue adjacent or distant to the tumor is also abnormal (Nonn et al., (2009) *Prostate* 69, 1470-1479). This field defect (also termed field effect) has been identified in colon and head and neck cancer, as well as prostate based on alterations in gene expression (YP, Y. (2004) *Journal of Clinical Oncology* 22; Chandran et al., (2005) *BMC Cancer* 5, 45) and genomic loss of imprinting (Agnieszka et al., (2009) *International Journal Of Oncology* 35, 87-96). Aberrant methylation patterns in the GSTP1, RARb2, APC and RASSFIA promoters have been detected in normal epithelial or stromal tissue adjacent to cancer (Aitchison et al., (2007) *Prostate* 67, 638-644; Hanson et al., (2006) *J. Natl. Cancer Inst.* 98, 255-261; Henrique et al., (2006) *Mol Cancer Res* 4, 1-8). These genes are altered in the tumor and represent a single gene approach to analyzing the field effect. These gene alterations may increase the proliferation or decrease cell death in epithelial cells, the cell of origin for prostate cancer. This may potentially underlie alterations in epithelial number in men whose prostates contain cancer elsewhere.

By use of the present invention, one can reassure men who have a negative biopsy that no cancer is present by measuring epithelial thickness or gland lumen roundness without additional future biopsies and avoid the complications directly associated with increasing the biopsy number and frequency. If a high epithelial thickness or low gland lumen roundness is detected, more detailed imaging with an MRI and endorectal probe and a more aggressive detection strategy requiring anesthesia and 30-50 biopsies will typically be undertaken to detect and/or characterize the disease. This approach is associated with additional risks associated with anesthesia, infection, bleeding and others, and is not performed routinely. In addition, it is likely these patients would be monitored much more closely. Applicants have demonstrated additional methods for the identification of prostate cancer field defects. See, e.g., U.S. Published Patent Application Nos. 2012/0135877, 2014/0296355, and 2018/0136215. Each published patent application is incorporated herein by reference as if set forth in its entirety.

In developing the present invention, the inventors have analyzed histologically normal tissues from men with and without prostate cancer utilizing automated quantitative image analysis to determine epithelial thickness or gland lumen roundness. The inventors associated an increased epithelial thickness or decreased gland lumen roundness with the presence of prostate cancer. Analysis of epithelial thickness or gland lumen roundness in tissue samples from patients will enhance the detection of prostate cancer.

By "histologically normal", we mean prostate tissue that has no evidence of disease in the specimen itself, based on standard morphologic and histochemical criteria used by pathology. By "normal" or "non-tumor associated (NTA)", we mean a prostate specimen that not only does not contain cancer itself, as defined by a pathologist, but also does not contain cancer elsewhere in the prostate. By "tumor associated (TA)", we mean a prostate specimen which does not show evidence of cancer, but is taken from a prostate with evidence of cancer in another location. One would appreciate that both "non-tumor associated" and "tumor associated" prostate specimens in this application are "histologically normal" prostate specimens. In one embodiment, histologically normal tissues are substantially free of prostatic intraepithelial neoplasia (PIN) or other pathological abnormalities. In one embodiment, histologically normal tissue samples are evaluated to exclude any cancer.

Within normal prostate tissues are glands defined by an interior lumen, or open space, surrounded by epithelial cells which are then surrounded by the stromal cells of the prostate tissue. Changes in the properties of the gland, the lumen within the gland, and the epithelial cells that make up the gland may be analyzed in relationship to the state and relative health of the prostate tissue.

The term "epithelial thickness," as used herein refers to the thickness of epithelium wall surrounding the gland lumens within the prostate section. Epithelial thickness can be measured, for example, as the average distance between a point along the lumen and a point on the nearest glandular border where the stromal cells begin. (See FIG. 3A for a sample measurement). In some embodiments, automated imaging of stained tissue is used to identify a given area as epithelial or stromal and the epithelial thickness is calculated as the distance from the gland lumen epithelial surface to the epithelial/stromal interface of the prostate tissue on the edge of the gland. In some embodiments, epithelial thickness is measured as the average epithelial thickness of at least 2, at least 3, at least 4, at least 5, at 6, at least 8, at least 10, at least 15, or at least 20 lumens measured in a patient sample.

The term "gland lumen roundness," as used herein refers to the quantitative value placed on the roundness or irregular shape of the lumen, or gap, within a gland present in the prostate tissue. Gland lumen roundness can be calculated, for example, by dividing the lumen surface area by the surface area of a circle with the same circumference. When measured by dividing the lumen surface area by the surface area of a circle with the same circumference, a roundness value of 1 indicates a perfectly circular lumen, while values closer to zero indicate irregular shape. In some embodiments, automated imaging of stained tissues is used to identify a given area as epithelial or stromal and the gland lumen roundness is calculated by dividing the surface are of the lumen by the surface area of a circle with the same circumference, wherein the lumen is defined by the gap in the epithelial cells in the glad and the circumference is measured on the interior edge of the epithelial cells boarding the lumen. In some embodiments, gland lumen roundness is measured as the average roundness of at least 2, at least 3, at least 4, at least 5, at 6, at least 8, at least 10, at least 15, or at least 20 lumens measured in a patient sample.

The term "epithelium" refers to layers of cells that line hollow organs and glands. It is also those cells that make up the outer surface of the body. Epithelial cells help to protect or enclose organs. All glands are made up of epithelial cells as in this situation in the prostate. Functions of epithelial cells include secretion, selective absorption, protection, transcellular transport, and sensing. The term "stromal" refers to cells that are connective tissue cells of any organ, for example in the uterine mucosa (endometrium), prostate, bone marrow, and the ovary. Stromal cells support the function of the parenchymal cells of that organ. Epithelial cells are the origin of prostate cancer. Fibroblasts and pericytes are among the most common types of stromal cells. The interaction between stromal cells and tumor cells is known to play a major role in cancer growth and progression.

EMBODIMENTS OF THE PRESENT INVENTION

In one embodiment, one can diagnose and/or treat prostate cancer in a human subject by measuring the epithelial thickness or gland lumen roundness in histologically normal tissue biopsy specimens taken from men who may have prostate cancer. Based on the results of the detection methods described herein, the subject may be diagnosed with prostate cancer and/or treated for prostate cancer via conventional therapies.

It is an advantage of the present invention that fewer biopsies are needed for the detection of prostate cancer. In a preferred embodiment, the measurement of an epithelial thickness or gland lumen roundness can be detected based on only 1-2 core biopsy specimens taken from anywhere in the prostate. In addition, in individuals who have had a negative biopsy but whose PSAs continue to rise, analysis of the previously obtained specimens for epithelial thickness or gland lumen roundness in histologically normal tissue will direct whether additional evaluation needs to be performed.

If the average epithelial thickness measured in the sample from a subject is increased relative to the epithelial thickness in a sample from a healthy, prostate tumor free subject, a more intensive biopsy set requiring anesthesia would be performed or the subject would be treated for prostate cancer. If not, the patient can be reassured. In some embodiments, the average epithelial thickness is increased by at least about 6% indicating associated prostate cancer. In some embodiments, the average epithelial thickness is increased by at least about 7%, at least about 8%, at least about 9%, at least about 10%, at least about 11% or at least about 12%. The average epithelial thickness may be measured from a single lumen in the sample or may be averaged over at least 2, at least 3, at least 4, at least 5, at least 8, at least 10, at least 15, or at least 20 lumens in the sample.

In some embodiments, if the epithelial thickness is higher than $3.00 \times 10^{-5}$ m, when measured using a VECTRA™ (Perkin Elmer, Waltham, Mass.) automated quantitative imagining system and inForm2.1.1 image analysis software, a more intensive biopsy set requiring anesthesia would be performed. If not, the patient can be reassured. In one embodiment, an epithelial thickness higher than about $3.00 \times 10^{-5}$ m (e.g., at least about $2.95 \times 10^{-5}$ m, $3.00 \times 10^{-5}$ m, $3.05 \times 10^{-5}$ m, $3.10 \times 10^{-5}$ m, $3.15 \times 10^{-5}$ m), when measured using a VECTRA™ (Perkin Elmer, Waltham, Mass.) automated quantitative imagining system and inForm2.1.1 image analysis software, is indicative of associated prostate cancer. In some embodiments, the epithelial thickness is between about $2.90 \times 10^{-5}$ m and $3.20 \times 10^{-5}$ m (e.g., between about $2.90 \times 10^{-5}$ m and $3.20 \times 10^{-5}$ m, $2.95 \times 10^{-5}$ m and $3.15 \times 10^{-5}$ m, $3.00 \times 10^{-5}$ m and $3.10 \times 10^{-5}$ m).

If the average gland lumen roundness measured in the sample from a subject is decreased by at least about 6% relative to the gland lumen roundness measured in a sample from a healthy, prostate tumor free subject, a more intensive biopsy set requiring anesthesia would be performed or the subject would be treated for prostate cancer. If not, the patient can be reassured. In some embodiments, the average gland lumen roundness is decreased by at least about 10% indicating associated prostate cancer. In some embodiments, the average gland lumen roundness is decreased by at least about 11%, at least about 12%, at least about 13%, at least about 14%, at least about 15% or at least about 16%. The average gland lumen roundness may be measured from a single lumen in the sample or may be averaged over at least 2, at least 3, at least 4, at least 5, at least 8, at least 10, at least 15, or at least 20 lumens in the sample.

In some embodiments, if the gland lumen roundness is measured by dividing the lumen surface area by the surface area of a circle with the same circumference and is less than 0.36, a more intensive biopsy set requiring anesthesia would be performed. If not, the patient can be reassured. In one embodiment, gland lumen roundness is measured by dividing the lumen surface area by the surface area of a circle with the same circumference and is less than about 0.36 (e.g., at most about 0.36, 0.35, 0.34, 0.33) and is indicative of associated prostate cancer. In some embodiments, the gland lumen roundness is between about 0.32 and 0.36 (e.g., between about 0.32 and 0.36, 0.33 and 0.35).

To examine the epithelial thickness or gland lumen roundness in histologically normal tissues, one would typically wish to obtain histologically normal tissue samples from a patient and prepare said tissue samples for microscopic analysis. Samples may be obtained from a prostate biopsy. In one typical embodiment, prostate tissue samples are obtained via standard transrectal ultrasound and biopsy protocols using an 18 gauge needle (Brooks et al. (2010) *J.Natl.Med.Assoc.* 102(5), 423-429). In another embodiment, prostate tissues are obtained from paraffin blocks of prostate biopsy samples that have already been obtained and examined.

Preparation of the tissue samples will involve staining the tissue samples with a stain specific to epithelial cells or staining that distinguishes epithelial cells from stroma. Any stain known in the art specific to epithelial cells may be used. Stains may include, but are not limited to, hematoxylin and eosin (H&E) stain; immunofluorescence staining for epithelial markers including cytokeratin, E-cadherin, keratin 8 or EpCam; immunofluorescence staining combined with stroma staining using Sirius red with picric acid; acidic or basic dyes including, but not limited to, Periodic acid-Schiff reaction (PAS), Masson's trichrome, van Gieson, Reticulin Stains, toluidine blue, chrome alum, isamin blue, nissl and methylene blue; or immunostaining (e.g. CD49A). In one embodiment, tissue samples are stained using H&E stain. In one embodiment, tissue samples are formalin fixed and paraffin embedded prior to staining.

In some embodiments, the stain is a high molecular weight cytokeratin. Cytokeratins are keratin proteins found in the intracytoplasmic cytoskeleton of epithelial tissue. They are an important component of intermediate filaments, expression of these cytokeratins within epithelial cells is largely specific to particular organs or tissues. After deparaffinizing and rehydrating the tissue section slide, boil the slide in sodium citrate for antigen retrieval. Permeabilize the section, block the non-specific binding with animal serum, and then stain the slide with anti-human pan-cytokeratin overnight at 4° C. in humidified chamber, wash off the slide and then add secondary antibody at room temperature for 1-2 hours. Finally apply DAPI to the slide for 5 minutes to reflect the total cell staining. Slide image is obtained using automated quantitative imaging system VECTRA™ system, and then analyzed using image software-inForm2.1.1. Epithelium % is calculated as the positive staining of cytokeratin to the total cell cumber (positive staining of DAPI).

Following staining, tissue samples may be imaged by any means known in the art. Tissue samples may be imaged manually or automatically. In some embodiments, the tissue is imaged and digitized using a microscope equipped with a camera or a digital microscope system. In some embodiments, tissue is imaged using a microscope and a slide scanner (e.g., a Huron™ slide scanner). In some embodiment, tissue samples are imaged automatically. In one embodiment, tissue samples are imaged using an automated quantitative imagine system. Automated quantitative image systems may include, but are not limited to VECTRA™ (Perkin Elmer, Waltham, Mass.), Aperio eSlide Manager (Leica Biosystems, Buffalo Grove, Ill.), TissueFAXS 220, TissueFAXS CONFOCAL PLUS 200 (TissueGnostics, Vienna, Austria), and the like.

Estimates of epithelium and stromal content in histologically normal prostate tissue samples or images of the prostate tissue samples may be done by any means known in the art. In one embodiment, the epithelial and stromal regions are estimated by semiquantitative visual review by one of skill in the art. In one embodiment, the epithelial and stroma regions are estimated by automated image analysis. In some embodiments, the epithelial and stroma regions are analyzed using one or more machine learning algorithms. For instance, image data can be input to one or more machine learning algorithms that have been trained to generate output as feature data that contain estimates of epithelial content, stromal content, tissue content, or combinations thereof.

The term "automated image analysis," as used herein refers to an automated method for the analysis and quantification of epithelium and stromal content in a tissue sample. The steps of automated image analysis using image analysis software may typically include (1) manual definition of epithelium, stromal, and background regions of the images, (2) training of the software to recognize epithelium, stromal, and background regions of the images as manually defined, (3) automated segmentation of images into epithelium, stromal and background regions, (4) quantification of the area of each of the epithelium, stromal, and background regions of the images using an algorithm specific to the software. Automated image analysis software may include, but are not limited to inForm2.1.1, StrataQuest 5.0 software, Aperio GENIE Image Analysis, and the like. In one embodiment, the automated image analysis software is inForm2.1.1. In one embodiment, the automated image analysis software is integrated within the automated quantitative image system.

As noted, in some embodiments image data can be input to one or more machine learning algorithms that have been trained to generate output as feature data containing estimates of epithelial content, stromal content, or both. In general, image data can include one or more images of a tissue sample from a patient. The tissue sample may often be an in vitro tissue sample (e.g., a tissue sample obtained via a biopsy).

Figure 4:
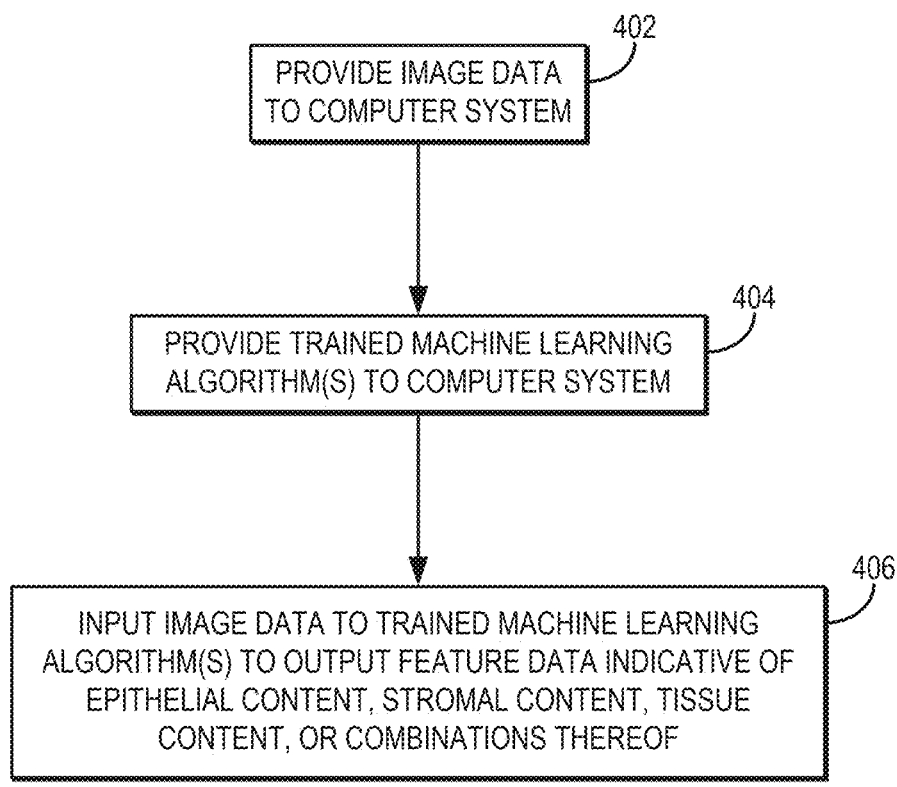

Referring now to FIG. 4, a flowchart is illustrated as setting forth the steps of an example method for generating feature data indicative of epithelial content, stromal content, or both, by inputting image data into one or more suitably trained machine learning algorithms. The method includes providing image data to a computer system, as indicated at step 402. The image data can be provided to the computer system by retrieving previously acquired image data from a memory or other suitable data storage device or medium. In other instances, the image data can be provided to the computer system by acquiring image data with an imaging system and communicating the image data from the imaging system to the computer system, which in some instances may form a part of the imaging system.

One or more trained machine learning algorithms are also provided to the computer system, as indicated at step 404. A machine learning algorithm can be provided to the computer system by retrieving a previously trained machine learning algorithm from a memory or other data storage device or medium. For instance, the architecture (e.g., number and types of layers or functions) and parameters (e.g., weights, biases), and so on, of a trained machine learning algorithm can be stored and retrieved. In other instances, providing a trained machine learning algorithm can include training the machine learning algorithm on appropriate training data. In either instance, the one or more machine learning algorithms are trained using training data that includes epithelial content data, stromal content data, or both. Such data may include labeled data, unlabeled data, or both.

Epithelial content data may, for instance, include images depicting epithelial cells and may include labels, annotations, or other data indicating epithelial content, such as epithelial thickness, number of epithelial cells, epithelial cell area, epithelial cell size, or other parameters, properties, or characteristics of epithelial cells depicted in the images.

Similarly, stromal content data may, for instance, include images depicting stromal cells and may include labels, annotations, or other data indicating stromal content, such as number of stromal cells, stromal cell area, stromal cell size, or other parameters, properties, or characteristics of stromal cells depicted in the images. The training data may also include other tissue data, such as images, labels, annotations, or other data indicating tissue content, such as gland lumen roundness or other parameters, properties, or characteristics of the tissue of interest.

The one or more machine learning algorithms can be trained on such training data using techniques known in the art. For instance, a gradient descent technique (e.g., stochastic gradient descent) could be used to train the machine learning algorithm based on the training data. As other examples, a momentum technique, a root mean square propagation (RMSProp), adaptive moment optimization (Adam), or other suitable training technique could be used.

The machine learning algorithm may be any suitable machine learning algorithm, such as a support vector machines (SVM) algorithm, k-nearest neighbors (k-NN) algorithm, a neural network, and so on. As one example, the machine learning algorithm can be a neural network, and may be a convolutional neural network (CNN). In these instances, the neural network can include one or more inputs. The inputs can be passed to one or more layers to generate output as the feature data. The one or more layers may include one or more hidden layers, convolutional layers, activation or nonlinear layers, dropout layers, pooling layers (e.g., max pooling layers), and so on. One or more of the layers in the neural network may be fully connected layers.

Referring still to FIG. 4, the image data are input to the trained machine learning algorithm, generating an output as feature data, as indicated at step 406. As an example in which the machine learning algorithm is a neural network, the image data can be input to one or more inputs in the trained neural network, generating output. The output from the input layer is passed to a first layer in the machine learning algorithm, such as a convolutional layer in a convolutional neural network, generating output. The output from this first layer is passed to a second layer, which in some instanced may be an output layer. More generally, the second layer will not be an output layer, but may be a hidden layer, a convolutional layer, an activation or nonlinear function layer, a dropout layer, a pooling layer, or the like. For instance, the second layer could be an activation or nonlinear layer that applies a suitable activation or nonlinear function to the output from the first layer. As an example, the activation or nonlinear function could be a rectified linear unit (ReLU), a sigmoid, or so on. The output generated by the second layer is then passed to the next layer in the neural network, generating output. This process is repeated for each layer in the neural network until the output layer generates output as the feature data containing epithelial content data, stromal content data, or both. As noted above, the feature data may also include tissue content data.

In general, the feature data generated by the machine learning algorithm contain qualitative or quantitative information about features of, or present in, the image data. For instance, as described above, the feature data can include information about the size, number, area, or other parameter, property, characteristic, or the like of epithelial cells, stromal cells, or tissues in a tissue sample depicted in the image data. The feature data can indicate epithelial content, stromal content, tissue content, or combinations thereof, which may include measurements, estimates, or predictions of epithelial thickness, gland lumen roundness, or so on.

In some instances, the feature data may include a classification of the tissue sample from which the image data were obtained. As an example, the machine learning algorithm can be trained to classify a tissue sample as being cancerous or non-cancerous based on the epithelial content, stromal content, tissue contents, or combinations thereof. As noted, a tissue sample can be classified in this manner based on estimates of epithelial thickness or gland lumen roundness. In one non-limiting example, images of histologically normal prostate tissue can be input to the trained machine learning algorithm in order to generate output that indicates a classification of the prostate tissue as being cancerous or non-cancerous. The machine learning algorithm in these examples is trained on training data that includes labeled or otherwise annotated data indicative of whether the tissue samples depicted in the training data are cancerous or non-cancerous. In some instances, the machine learning algorithm may be trained using unsupervised learning. The feature data may also include a tumor grade.

Methods described herein are used to determine the epithelial thickness or gland lumen roundness in a sample of histologically normal prostate tissue. It is understood in the art that the particular measurement techniques, imaging systems, and analysis software used may generate different relative epithelial thickness or gland lumen roundness measurements for a single tissue sample. The percentages and values as quoted herein reflect the percentage as calculated using a VECTRA™ (Perkin Elmer, Waltham, Mass.) automated quantitative imagining system and inForm2.1.1 image analysis software. In one embodiment, an epithelial thickness greater than $3.00 \times 10^{-5}$ m or a gland lumen roundness less than 0.36, as measured by the method described in the previous sentence, is indicative of prostate cancer. In one embodiment an epithelial thickness greater than $3.05 \times 10^{-5}$ m is indicative of prostate cancer. In another embodiment, an epithelial thickness greater than $3.10 \times 10^{-5}$ m is indicative of prostate cancer. In one embodiment, a gland lumen roundness less than 0.35 is indicative of prostate cancer. In another embodiment, a gland lumen roundness less than 0.34 is indicative of prostate cancer. In some embodiments, an increase in epithelial thickness of at least about 6% and a decrease in gland lumen roundness of at least about 10%, relative to the epithelial thickness and gland lumen roundness measured in a sample from a healthy, prostate tumor-free subject, is indicative of prostate cancer.

Thus, as described in the present disclosure, methods for treating prostate cancer in a human subject may include obtaining histologically normal prostate tissue from the subject and quantifying epithelial thickness in that tissue. Quantifying the epithelial thickness can include obtaining image data of the tissue (e.g., with or without staining the tissue) and inputting the image data to a machine learning algorithm trained as described above. The output of the trained machine learning algorithm can be feature data containing the quantified epithelial thickness. The human subject can be treated, then, when the epithelial thickness estimated in the feature data is increased by at least about 6%.

As also described in the present disclosure, methods for treating prostate cancer in a human subject may include obtaining histologically normal prostate tissue from the subject and quantifying gland lumen roundness in that tissue. Quantifying the gland lumen roundness can include obtaining image data of the tissue (e.g., with or without staining the tissue) and inputting the image data to a machine learning algorithm trained as described above. The output of the trained machine learning algorithm can be feature data containing the quantified gland lumen roundness. The human subject can be treated, then, when the gland lumen roundness estimated in the feature data is decreased by at least about 10%.

Figure 5:
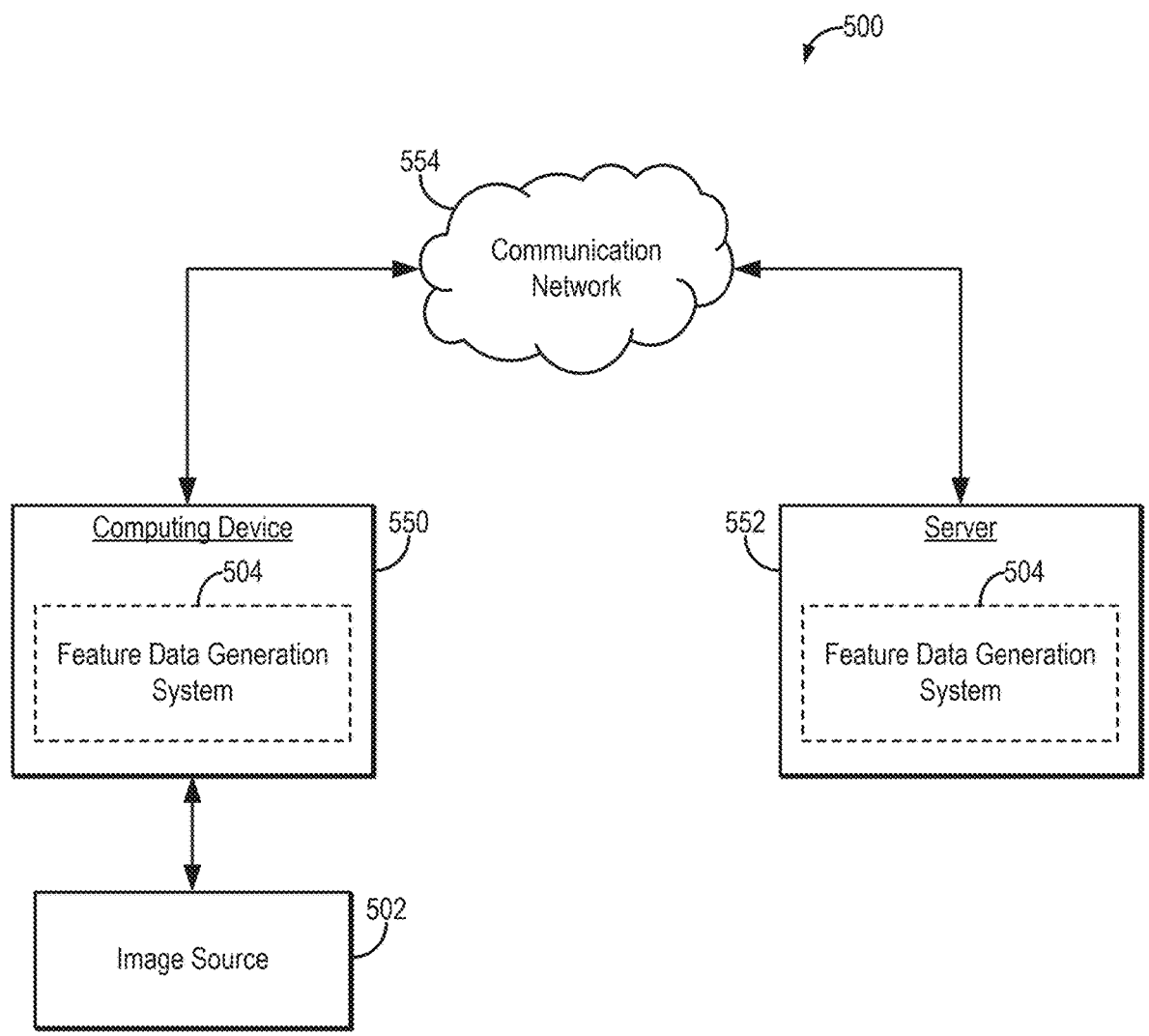
FIG. 5 is a block diagram of an example system that can implement image analysis algorithms, including machine learning algorithms trained to generate output as feature data indicative of epithelial content, stromal content, tissue content, or combinations thereof.

Referring now to FIG. 5, an example of a system 500 for generating feature data (e.g., epithelial content data, stromal content data, tissue content data) in accordance with some embodiments of the systems and methods described in the present disclosure is shown. As shown in FIG. 5, a computing device 550 can receive one or more types of data (e.g., image data) from image source 502, which may be a tissue sample image source. In some embodiments, computing device 550 can execute at least a portion of a feature data generation system 504 to generate epithelial content data, stromal content data, or tissue content data from image data received from the image source 502.

Additionally or alternatively, in some embodiments, the computing device 550 can communicate information about data received from the image source 502 to a server 552 over a communication network 554, which can execute at least a portion of a feature data generation system 504 to generate epithelial content data, stromal content data, or tissue content data from image data received from the image source 502. In such embodiments, the server 552 can return information to the computing device 550 (and/or any other suitable computing device) indicative of an output of the feature data generation system 504 to generate epithelial content data, stromal content data, or tissue content data from image data received from the image source 502.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image source 502 can be any suitable source of image data (e.g., measurement data, images reconstructed from measurement data), such as an imaging system used to image a tissue sample, another computing device (e.g., a server storing image data), and so on. In some embodiments, image source 502 can be local to computing device 550. For example, image source 502 can be incorporated with computing device 550 (e.g., computing device 550 can be configured as part of a device for capturing, scanning, and/or storing images). As another example, image source 502 can be connected to computing device 550 by a cable, a direct wireless link, and so on. Additionally or alternatively, in some embodiments, image source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
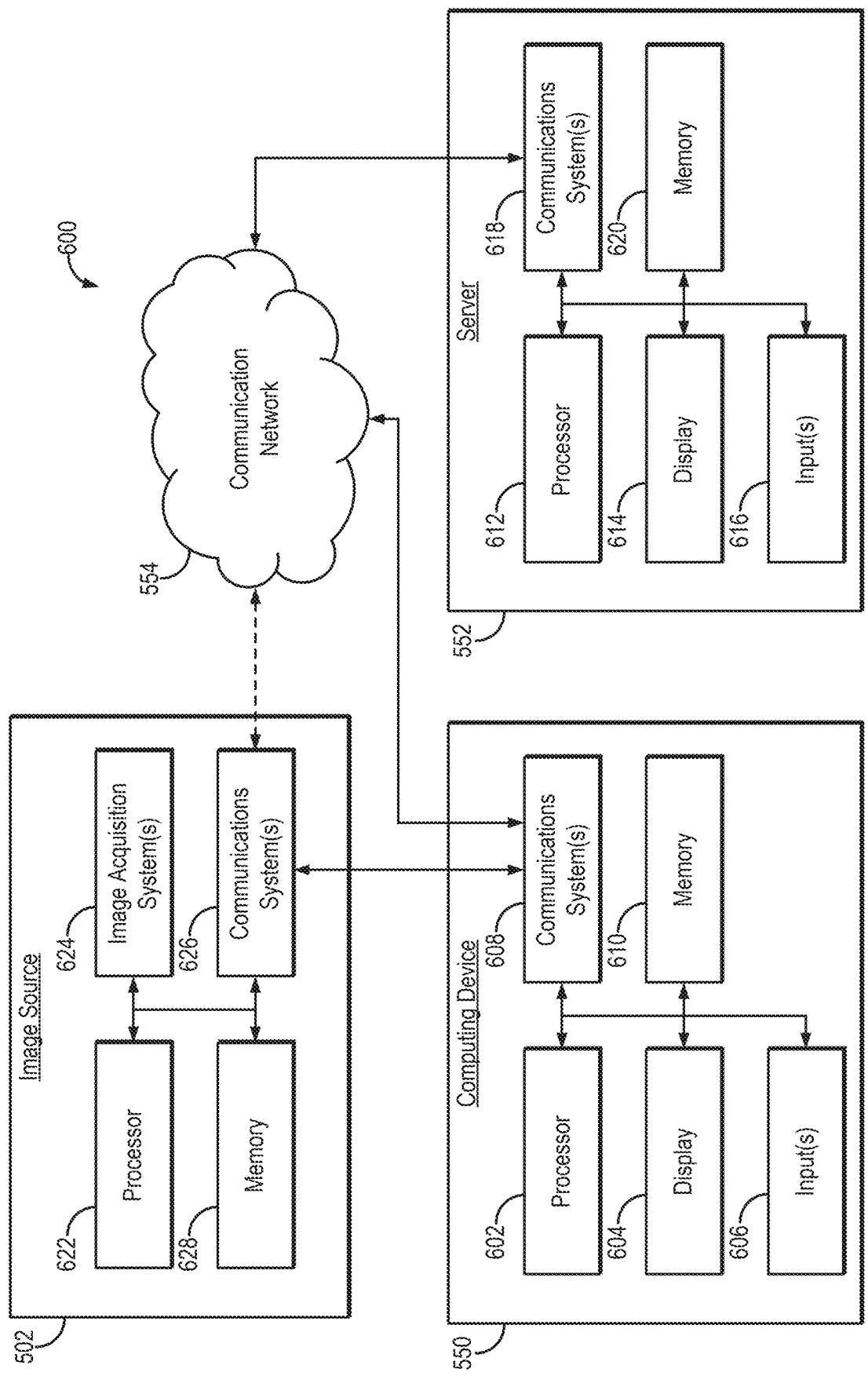
FIG. 6 is a block diagram of example hardware that can be implemented in the system of FIG. 5.

Referring now to FIG. 6, an example of hardware 600 that can be used to implement image source 502, computing device 550, and server 554 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include a camera, other optical imaging system, or other imaging system that can obtain images of a tissue sample. Additionally or alternatively, in some embodiments, one or more image acquisition systems 624 can include any suitable hardware, firmware, and/or software for coupling to and/or controlling operations of an imaging system. In some embodiments, one or more portions of the one or more image acquisition systems 624 can be removable and/or replaceable.

Note that, although not shown, image source 502 can include any suitable inputs and/or outputs. For example, image source 502 can include input devices and/or sensors that can be used to receive user input, such as a keyboard, a mouse, a touchscreen, a microphone, a trackpad, a trackball, and so on. As another example, image source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The Examples focus on a preferred method, but one of skill in the art would understand that other methods would be suitable.

EXAMPLES

The embodiment described herein demonstrates the measurement of features of epithelium and stroma in histologically benign prostate tissue samples. Utilizing digital imaging, benign H&E biopsy slides were analyzed using InForm2.1.1 and custom Matlab software to measure features of epithelium and stroma in a discovery cohort of 59 patients. The prognostic nature of predictive features were validated in a subsequent blinded validation set(n=116 subjects). Epithelial cell number was quantified using Vectra™ after epithelial immunostaining using a pancytokeratin marker.

The "field defect" is a concept wherein histologically benign appearing tissue exhibits neoplastic molecular changes. Its identification in prostate cancer (PCa) (1-4) explains the multifocal nature of the disease and its association with age.(5,6) Epigenetic changes, including DNA methylation and alterations in genomic imprinting, have been identified in histologically benign appearing tissue from men with PCa.(7) These changes are useful in the detection of the disease in men with negative biopsy tissue. (8)

These molecular findings suggest underlying alterations in the cell morphology of solid organ tissue present in patients with cancer. Many prostate lesions have 'large gland' morphology with gland size greater than benign glands, complex glandular architecture and significant cytological atypia.(9) The most common and clinically important lesion with large gland morphology is high-grade prostatic intraepithelial neoplasia (HGPIN) that can associate with increased prostate cancer (PCa) risk.(10) Similar ductal changes also occur in the benign breast associated with the presence of cancer.(11) Loss of intervening stroma is also seen with the development of histologic PCa leading to an increased epithelial to stromal ratio.(12) With the advent of high resolution digital images and computer processing capacity subtle alterations in the architecture of benign tissues are being found. A recent analysis of benign breast tissues reveals stromal area decreases and adipose area increases with aging. Lack of this age-related regression of mammary epithelial, termed postmenopausal involution, is associated with increased breast cancer risk.(13)

Application of computerized morphometric analysis represents a new paradigm in pathology, permitting rapid and cost-effective extraction of image-based features from histologic tissue.(14) Previous studies examining PCa histology have focused on characterizing the differences between benign and cancer glands.(15,16) In contrast, the current work applies computerized morphometric analysis of H&E stained benign prostate biopsy cores Materials and Methods Samples—Benign prostate biopsies from patients with an elevated PSA were analyzed from a sequential dataset that included non-tumor associated (NTA, n=89) and tumor associated (TA) cases (n=83). TA cases underwent radical prostatectomy to confirm cancer elsewhere in the prostate. NTA cases underwent ≥2 previous negative biopsies to rule out cancer. An independent validation cohort subsequently tested included 179 benign mid-prostate biopsy cores from 116 patients (92 TA and 87 NTA). Mid-prostate biopsy cores were utilized based on training set results. Biopsy cores were obtained from the peripheral zone using an ultrasound guided standard 10-14 core biopsy template.

To address whether the epithelial component changes with age, two tissue microarrays (TMA) from 37 cancer-negative cystoprostatectomy specimens were stained and analyzed. Samples were obtained from patients ranging from 28 to 86 years old (median 66 years). All protocols were approved by the Institutional Review Board at the University of Wisconsin and performed in accordance with institutional and national guidelines. Informed consent was obtained from all participants.

Immunohistochemistry—Benign mid-prostate biopsy cores from 60 patients (30 TA and 30 NTA) were randomly selected from the validation set for automated immunohistochemical (IHC) staining with the epithelial marker pan-cytokeratin (AE1/3 clone, Dako(Agilent)). After heat-induced epitope retrieval was performed and 100 μl of AE1/AE3 diluted 1:1000 applied, anti-Mouse HRP and Discovery ChromoMap were used for development [17] and imaging analysis performed.

Automated image acquisition and analysis—Paraffin-embedded cancer-negative prostate cores were stained with hematoxylin and eosin (H&E) and reviewed to exclude HGPIN, atypical small acinar proliferation, and other pathologic abnormalities associated with cancer presence by a fellowship-trained genitourinary pathologist (W.H.). H&E and IHC slides were then imaged with the Vectra™ platform and analyzed with InForm version 2.1.1 software (Perkin Elmer) as previously described. [17, 18] Briefly, a spectral library for each chromogen was created. Algorithms for tissue and subcellular compartment separation were created by machine learning with precision above 95% (FIG. 1A). Ten percent of the image dataset that represents heterogeneity of the biopsy tissue morphology was selected to create each algorithm. The epithelial area, stromal area, total tissue area, epithelial cell number (pan-CK positive cell number), and total cell number were calculated.

Figures 3A, 3B, 3C, 3D, 3E, 3F:
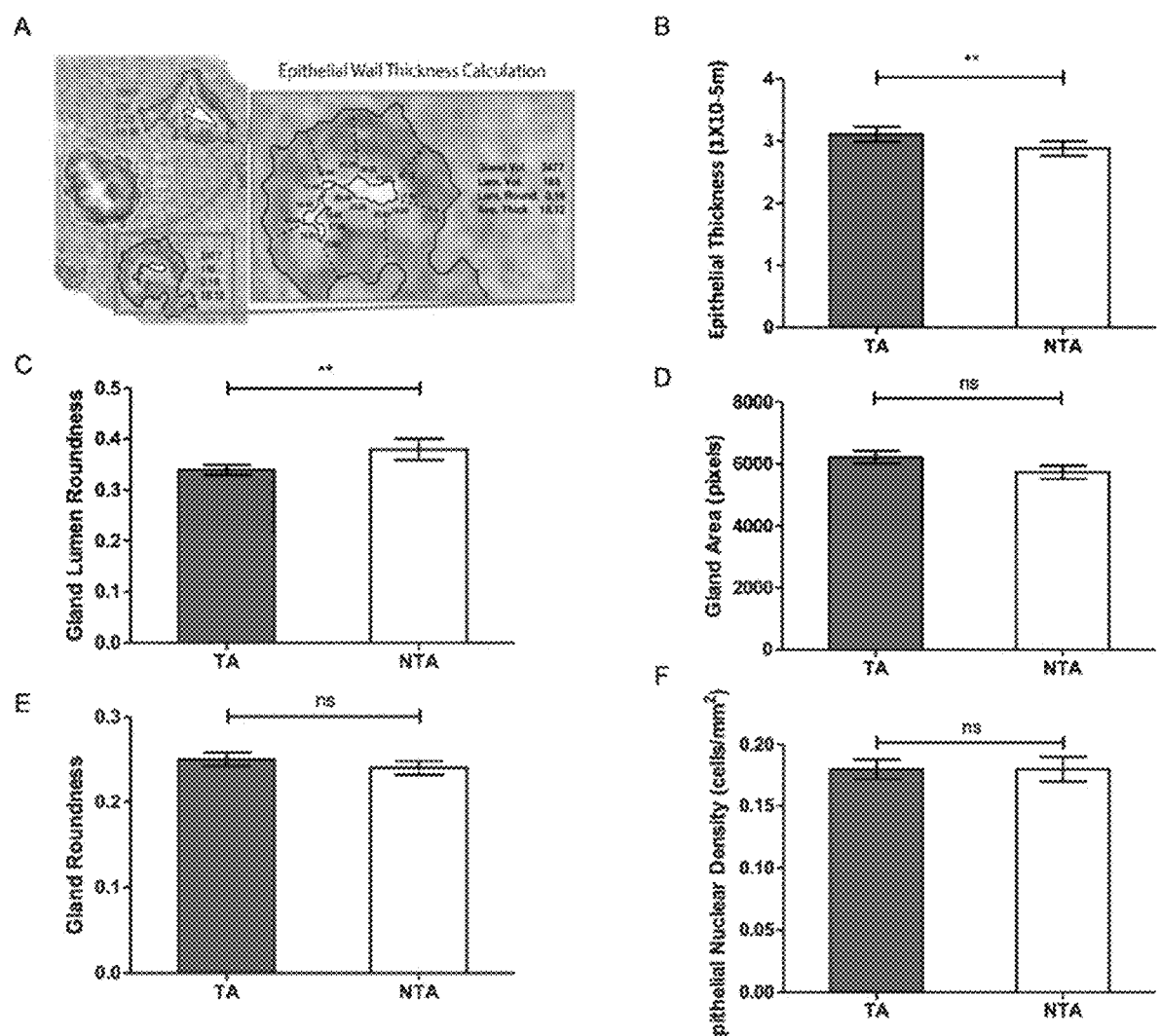
FIGS. 3A-3F show quantitative histologic data obtained with custom Matlab code (Mathworks, Natick, Mass.) using images from the H&E stained cancer negative prostate biopsy cores.

Epithelial thickness calculation—The digital images from the H&E stained training and validation set were additionally processed using custom Matlab code (Mathworks, Natick, Mass.) to segment each individual gland.(19) Color based intensity segmentation followed by morphometric filters identified individual lumen within individual glandular walls. The distance between each point along the surface of the lumen and along the surface of the epithelial wall was calculated and the minimum assigned to each point. The epithelial thickness for each lumen was calculated as an average of these values. This iterative procedure was done on each of the glands identified within each biopsy core. Gland lumen roundness was calculated by dividing the lumen surface area by that of a circle with the same circumference. A roundness value of 1 indicates a perfectly circular lumen, while values closer to zero indicate irregular shapes (FIG. 3A). The nuclear density of each gland was also calculated by segmenting the nuclei from the remainder of the epithelium and dividing by the total area.

Statistical Analysis—Clinical and pathologic variables were obtained for each subject. One-way ANOVA was used to compare epithelial area, epithelial to stromal ratio, and epithelial cell number between TA and NTA. A receiver operating curve (ROC) was generated and the area under the curve (AUC) calculated for each independent analysis. Spearman and Pearson Correlation coefficients were calculated to determine the association between epithelial area and pathologic variables. A one-way repeated measures ANOVA was calculated to compare epithelial area across multiple biopsy samples from the same patient. Statistical analysis was performed with STATA®. Generalized estimating equation modeling was performed on the epithelial thickness, gland lumen roundness, gland area, outer gland roundness, and epithelium nuclear density values. Significant results were then tested in a separate validation set.

Results

Patient and histologic characteristics—H&E stained biopsy slides collected as part of a trial examining an epigenetic marker in the benign tissue of men with PCa were digitally imaged and analyzed using the Vectra™ platform. Morphometric analysis of the epithelial and stromal areas using InForm2.1.1 software (Perkin Elmer) was performed on two histologically negative biopsies for each patient. Clinical data are detailed in Table 1. NTA patients have more previous cancer negative biopsies compared to TA because of study requirements to exclude cancer. NTA prostate size is greater in the training (39.4 g versus 47.8 g, p=0.02) and validation sets (44.0 g versus 52.1 g, p=0.04) consistent with PSA-driven screening trials (ref). For the TA group, Grade Groups 1-3 are the most common cancer histology (Table 2).

TABLE 1

Clinical features of training and validation study groups from patients who had no cancer (NTA) and cancer (TA) in other areas of the prostate.

| | Training | | p-value | Validation | | p-value |
|---|---|---|---|---|---|---|
| | TA | NTA | | TA | NTA | |
| Patients, n | 32 | 27 | — | 52 | 64 | — |
| Samples, n | 83 | 89 | — | 92 | 87 | — |
| Region Noted in Samples, n (%)^ | 76 (92) | 75 (84) | — | 92 (100) | 87 (100) | — |
| Age (years) | 60.9 (51-68) | 60.6 (54-71) | 0.77 | 64.8 (51-88) | 61.7 (36-76) | 0.04 |
| PSA (ng/mL)* | 6.5 (2.4-11.7) | 7.6 (4.0-15.0) | 0.12 | 13.2 (0.66-138.0) | 6.5 (0.5-20.9) | 0.03 |
| Prostate Size (g) | 39.4 (19.0-56.7) | 47.8 (26.3-85.0) | 0.02 | 44.0 (14.1-99.1) | 52.1 (18.0-116.0) | 0.04 |
| PSA Density (ng/mL/g)* | 0.16 (0.08-0.28) | 0.17 (0.07-0.40) | 0.44 | 0.29 (0.03-2.19) | 0.14 (0.01-0.40) | 0.005 |

°Ultrasound determined prostate size;
*Some data missing from individual patients;
^Some patients did not have biopsy location noted by sextant;
Tumor associated (TA), Non-Tumor Associated (NTA), Prostate Specific Antigen (PSA); All data represented as mean (range) unless stated otherwise.

TABLE 2

Pathologic features of training and validation study groups from patients who had no cancer (NTA) and cancer (TA) in other areas of the prostate.

| | Training | | | Validation | | |
|---|---|---|---|---|---|---|
| | TA | NTA | p-value | TA | NTA | p-value |
| % of Biopsy Cores Involved | 27.0 (0.0-60.0) | — | — | 23.3 (5.0-67.0) | — | — |
| Max % of Biopsy Core Involved*° | 47.5 (1.0-100.0) | — | — | 36.9 (1.0-100.0) | — | — |
| Biopsy Grade Group, n (%)* | | | | | | |
| 1 | 6 (19.4) | — | — | 23 (44.2) | — | — |
| 2-3 | 19 (61.2) | — | — | 17 (32.7) | — | — |
| 4-5 | 6 (19.4) | — | — | 12 (23.1) | — | — |
| Final Specimen Grade Group, n (%)* | | | | | | |
| 1 | 1 (3.1) | — | — | 4 (17.4) | — | — |
| 2-3 | 26 (81.3) | — | — | 14 (60.9) | — | — |
| 4-5 | 5 (15.6) | — | — | 5 (21.7) | — | — |
| Tumor volume (%)* | 9.8 (6.2) | — | — | 12.2 (10.8) | — | — |
| Positive Margins, n (%)* | 7 (21.9) | — | — | 3 (13.0) | — | — |
| ExtraCapsular Extension, n (%)* | 6 (18.8) | — | — | 4 (17.4) | — | — |

TABLE 2-continued

Pathologic features of training and validation study groups from
patients who had no cancer (NTA) and cancer (TA) in other areas of the prostate.

|  | Training | | | Validation | | |
|---|---|---|---|---|---|---|
|  | TA | NTA | p-value | TA | NTA | p-value |
| Pathologic Stage, n (%)* | | | | | | |
| T2a | 3 (9.4) | — | — | 4 (17.4) | — | — |
| T2b | 1 (3.1) | — | — | 0 (0) | — | — |
| T2c | 21 (65.6) | — | — | 14 (60.9) | — | — |
| T3a | 5 (15.6) | — | — | 4 (17.4) | — | — |
| T3b | 2 (6.3) | — | — | 1 (4.3) | — | — |

*Some data missing from individual patients;
°Maximum percentage of a single biopsy core involved with cancer;
Tumor Associated (TA), Non-Tumor Associated (NTA), Prostate Specific Antigen (PSA); All data represented as mean (range) unless stated otherwise.

Increased epithelial to stromal and epithelial to total area in tumor-associated benign tissues—Computer-based automated imaging finds no difference in the epithelial area as measured by absolute pixel number between TA and NTA biopsies for the complete group (p=0.28) (Table 3). However, stroma demonstrates a greater area in the NTA compared to TA (p=0.001). The ratio of epithelial to total area (Epi/Tot) or epithelial to stromal area (Epi/Str) is of greater significance as this adjusts for variations in total tissue area. Epi/Tot is increased in TA compared to NTA (44.9±1.4% and 38.8±1.1% p=0.0006, respectively). (FIG. 1B, Table 4). The AUC for predicting cancer is 0.65 (95% confidence interval (CI): 0.57-0.74). Epi/Str in TA (0.95±0.07) compared to NTA (0.69±0.04) is also greater (p=0.002) and generates an AUC of 0.62 (FIG. 1C).

Biopsy tissue is obtained primarily from the peripheral zone where PCa arises the majority of the time. Biopsy region may determine the amount of peripheral zone tissue present, with enriched samples from the lateral crescents of the mid-prostate.[12, 20] Regional analysis of biopsies were available from the majority of samples. Mid-prostate biopsies show the greatest differences in Epi/Tot between TA compared to NTA (46.4±2.4% and 39.0±1.9%, respectively p=0.02) (FIG. 1D), and in Epi/Str between TA (1.03±0.13) compared to NTA (0.70±0.07, p=0.03).

TABLE 3

Absolute epithelial, stromal, and total biopsy areas measured by pixel number for tumor
associated (TA) and non-tumor associated (NTA) histologically benign prostate biopsies.

|  | Epithelial Area (pixel number $\times 10^6$) | | | Stromal Area (pixel number $\times 10^6$) | | | Total Biopsy Area (pixel number $\times 10^6$) | | |
|---|---|---|---|---|---|---|---|---|---|
| Mean (SE) | TA | NTA | p-value | TA | NTA | p-value | TA | NTA | p-value |
| Training All | 0.91 (0.04) | 0.99 (0.07) | 0.28 | 1.11 (0.07) | 1.56 (0.10) | 0.0009 | 2.05 (0.09) | 2.55 (0.16) | 0.008 |
| Training RS | 0.87 (0.06) | 0.81 (0.07) | 0.50 | 1.07 (0.09) | 1.28 (0.09) | 0.16 | 1.94 (0.11) | 2.09 (0.12) | 0.49 |
| Apex | 0.85 (0.08) | 0.84 (0.07) | 0.93 | 1.15 (0.12) | 1.38 (0.13) | 0.21 | 2.00 (0.16) | 2.22 (0.14) | 0.36 |
| Mid | 0.89 (0.06) | 0.82 (0.08) | 0.44 | 1.00 (0.07) | 1.29 (0.07) | 0.004 | 1.89 (0.09) | 2.11 (0.12) | 0.14 |
| Base | 0.88 (0.05) | 0.76 (0.06) | 0.14 | 1.05 (0.08) | 1.18 (0.08) | 0.28 | 1.94 (0.09) | 1.94 (0.11) | 0.98 |
| Validation* | 0.92 (0.04) | 0.91 (0.04) | 0.86 | 1.06 (0.05) | 1.26 (0.06) | 0.01 | 1.98 (0.07) | 2.17 (0.08) | 0.09 |

*Validation set utilizes mid-prostate biopsies only. Known region-specific (RS) sextant samples.

TABLE 4

Percentage of epithelial area to total tissue area and
the epithelial to stromal area ratio for tumor associated (TA) and
non-tumor associated (NTA) cancer negative prostate biopsies.

|  | Epithelial/Total (%) | | | Epithelial/Stromal | | |
|---|---|---|---|---|---|---|
| Mean (SE) | TA | NTA | p-value | TA | NTA | p-value |
| Training | 44.9 (1.4) | 38.8 (1.1) | 0.0006 | 0.95 (0.07) | 0.69 (0.04) | 0.002 |
| Apex | 42.9 (2.4) | 38.8 (2.8) | 0.29 | 0.85 (0.10) | 0.68 (0.09) | 0.28 |
| Mid | 46.4 (2.4) | 39.0 (1.9) | 0.02 | 1.03 (0.13) | 0.70 (0.07) | 0.03 |
| Base | 45.4 (2.2) | 39.9 (2.2) | 0.08 | 0.98 (0.16) | 0.76 (0.08) | 0.18 |
| Validation* | 47.3 (1.3) | 41.8 (1.4) | 0.004 | 1.02 (0.06) | 0.81 (0.05) | 0.004 |

*Validation set utilizes mid-prostate biopsies only.

Figures 2A, 2B, 2C, 2D:
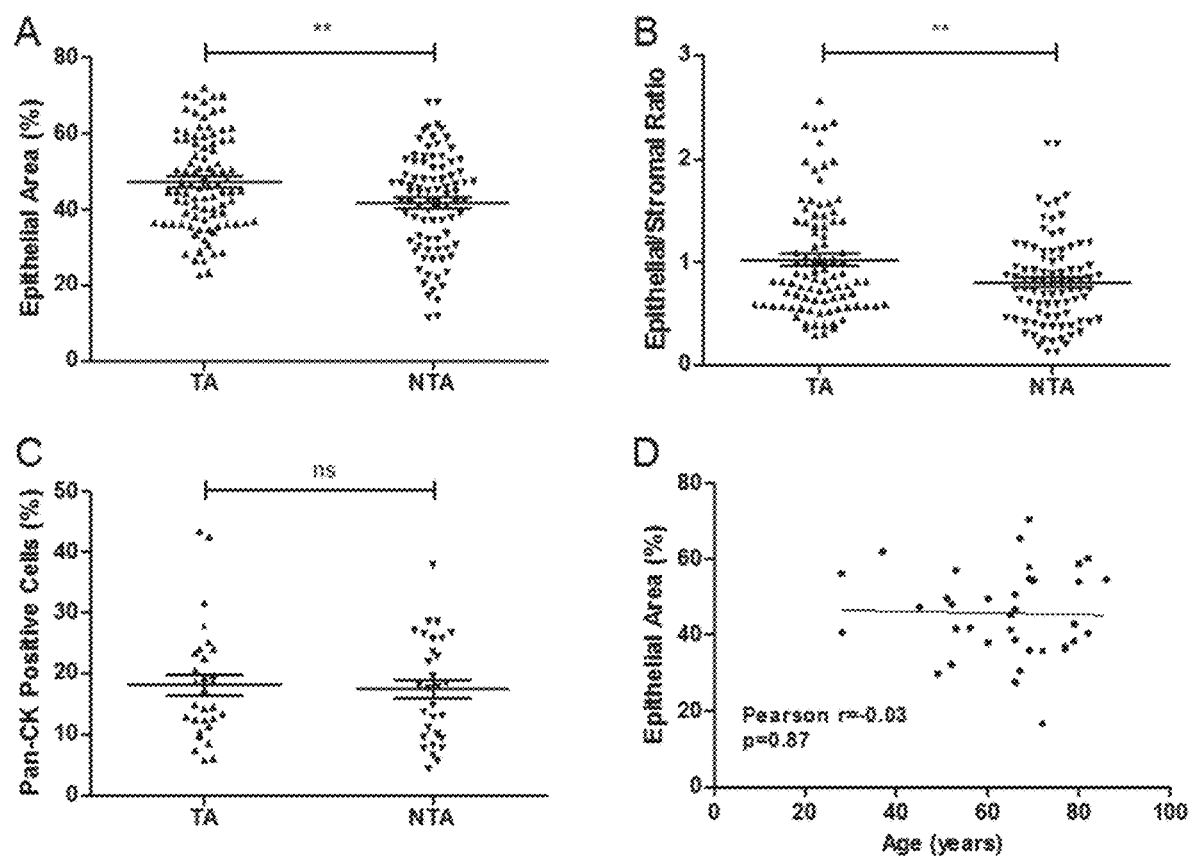
FIGS. 2A-2D show quantitative histologic data of validation set (n=179) obtained with InForm2.1.1 software (Perkin Elmer) using H&E stained cancer negative mid prostate biopsy cores.

Measurements in validation set—For blinded validation, we utilized mid-biopsy cores given our previous results. The epithelial area again is not significantly different between TA and NTA (p=0.86) (Table 3). Epi/Tot for TA (n=92, 47.3±1.3%) is greater than NTA (n=87, 41.8±1.4%, p=0.004; AUC 0.62, 95% CI: 0.54-0.70) (FIG. 2A, Table 4). The stromal area decreases in TA ($1.06 \times 10^6 \pm 0.05 \times 10^6$ pixels) compared to NTA ($1.26 \times 10^6 \pm 0.06 \times 10^6$ pixels; p=0.01) (Table 3). The mean±SE Epi/Str ratio for TA (1.02±0.06) compared to NTA (0.81±0.06) is also greater (p=0.004) (FIG. 2B).

No association with Epi/Tot and Grade Group (Spearman r=−0.01, p=0.87) or stage (Spearman r=−0.03, p=0.82) is observed. Prostate size varies between the comparison populations (Table 1). Controlling for prostate size, the Epi/Tot area did not vary with prostate size (training Pearson r=0.09, validation Pearson r=0.066). Molecular heterogeneity exists across the peripheral prostate with cancer [21]. To assess the uniformity of these imaging differences, we analyzed the Epi/Tot area between separate biopsies from the same patient and find little variation (training p=0.08, validation p=0.09).

Increased epithelial thickness and decreased gland lumen roundness—We questioned whether increased cell number might explain these image differences. Pan-cytokeratin (pan-CK) staining of individual epithelial cells in 30 TA and 30 NTA samples demonstrate no increase in absolute epithelial cell number in TA (n=30, $2.25 \times 10^4 \pm 0.23 \times 10^4$ pan-CK positive cells) compared to NTA (n=30, $2.16 \times 10^4 \pm 0.22 \times 10^4$ pan-CK positive cells, p=0.79). We found no difference in epithelial cell number as a percentage of total cell number in TA (18.1±1.7%) compared to NTA (17.4±1.6%, p=0.75) (FIG. 2C). Matched H&E stained biopsies again confirmed increases in the Epi/Tot area for TA (n=30, 44.6±2.3%) compared to NTA (n=30, 36.8±2.5%, p=0.03) for this subgroup.

Other features of epithelial architecture were analyzed to explain the increase in relative epithelial area. A custom Matlab code (Mathworks, Natick, Mass.) was used to examine other features. We demonstrate an increase in the epithelial thickness in TA (n=62, $3.11 \times 10^{-5} \pm 0.12 \times 10^{-5}$ m) compared to NTA (n=50, $2.88 \times 10^{-5} \pm 0.12 \times 10^{-5}$ m, p=0.006) (FIG. 3B), consistent with the increased epithelial area. Additionally, we observe decreased prostate gland lumen roundness between TA (0.34±0.01) and NTA (0.38±0.02, p=0.001) (FIG. 3C). Other features such as overall gland area (FIG. 3D), outer gland roundness (FIG. 3E), and epithelial nuclear density (FIG. 3F) do not significantly differ (p=0.10, p=0.70, p=0.51).

Epithelial content and age—Given reports of age-related changes in breast architecture[22], and the known association of PCa with age,[5, 6] we examined whether an association between epithelial area and age was present using a separate TMA from benign cystoprostatectomy specimens. We observed no association between Epi/Tot area with age (Pearson r=−0.03, p=0.87) (FIG. 2D). Biopsies from the training and validation sets were combined (n=351) and no association between Epi/Tot area and age was observed (Pearson r=−0.02, p=0.67).

Discussion

A molecular epigenetic field of susceptibility has been demonstrated in multiple cancers, including prostate.[5, 7] Subtle histologic changes not observed by the human eye can be detected by computerized morphometric analysis. The majority of these comparisons have been performed between benign and malignant glands to assist in the diagnosis and grading of cancer.[16, 23] We demonstrate for the first time that increases in epithelial area and epithelial thickness are associated with the presence of PCa from apparent histologically benign tissue.

A number of image features were examined, and a larger epithelial to total and epithelial to stromal area ratios conferred the strongest association with the presence of cancer. In archival literature, imaging of cancer glands using fractional dimension analysis and other software demonstrated increased complexity, irregularity, and epithelial amount in malignant compared to benign glands.[16, 23] Cancer specimens have a decrease in stroma between epithelial (cancer) glands, which is a hallmark of the disease. In radical prostatectomy specimens, more susceptible cancer populations trended towards lower stromal to epithelial ratios suggesting an important role for stroma. Notably, the importance of prostate stroma-epithelial interactions in cancer initiation, growth and progression is well established.[24, 25] Non-tumor patients were not examined. Notably, the current study is unique in focusing on histologically benign tissue between patients with and without malignancy.

To further interrogate this increase in epithelial gland area, we examined epithelial cell number. Increased epithelial cell number is a component of HGPIN, which may be associated with some PCa.[26] Pan-cytokeratin specifically stains epithelial structures, isolating the pathologically relevant prostate glandular architecture.[15] IHC staining with pan-cytokeratin did not detect differences in epithelial cell number between TA and NTA biopsies.

To further characterize the increased epithelial component, a color-based intensity segmentation analysis with morphometric filtering was used to identify individual gland lumens. This approach uses a program (MatLab) to optimize intensity contrast that highlights morphology features of the individual glands. We observed an increase in epithelial thickness (p=0.006) and decrease in gland lumen roundness (p=0.001) in TA compared to NTA. Although PCa compared to benign tissue typically contains smaller glands, "large gland" morphology is observed.[9] This large gland morphology may resemble adjacent benign glands architecturally, but with increased cell size, and is seen in HGPIN, PIN-like carcinoma, and intraductal carcinoma. These suggest larger more irregular epithelial cells arise in patients with cancer that underlies the increase in epithelial area.

PCa arises in spatially distinct regions, most commonly the peripheral zone.[27] A previous study comparing standard 12-core transrectal biopsies to radical prostatectomy specimens demonstrated the diagnostic accuracy for PCa detection was significantly different between biopsies obtained from the apex (55.7%), mid (60.9%), and base (64.2%).[28] These results may be due to increased peripheral zone sampling from biopsies obtained from the mid and base regions. Our results demonstrate the largest differences in epithelial area from mid-prostate biopsies (p=0.02). We conducted a second independent validation and IHC staining using biopsies obtained from the mid-prostate based on these results. The epithelial area (47.3% versus 46.4%) and epithelial to stromal ratio (1.02 versus 1.03) of the independent validation set were similar to the training set from the same region.

The risk of PCa increases markedly with age.[29] We sought to determine if the increase in epithelial area associated with TA tissue is an age-related phenomenon. We did not find an association between age and epithelial area in cancer-negative cystoprostatectomy specimens from patients' 28-86 years old. Notably, these were cancer-negative specimens, suggesting the epithelial area may be maintained in patients without cancer. Similarly, epigenetic features in the benign prostate tissue of patients without cancer are more maintained with aging than those with cancer.[5, 6] These data further support the hypothesis that the increased epithelial area is associated with a pre-neoplastic alteration.

The training NTA cases underwent ≥2 previous negative biopsies to rule out cancer. Although all patients had at least 2 years of follow-up, and 62% had negative MRI results, not all cancers may be detected. These criteria also cause imbalance with regard to gland size and PSA between groups, a common finding in biomarker studies of benign prostate tissue.[7] Imaging does not always recognize artifact, such as tissue folds, although an effort to remove these imaging distortions was undertaken. Finally, the variability in peripheral zone amounts between biopsy locations may generate error. Enriching for the peripheral zone or excluding transition zone tissue may improve the diagnostic ability, as evident with use of the mid-prostate biopsies.

REFERENCES

[1] Aitchison A, Warren A, Neal D, Rabbitts P. RASSF1A promoter methylation is frequently detected in both pre-malignant and non-malignant microdissected prostatic epithelial tissues. Prostate. 2007; 67:638-44.

[2] Hanson J A, Gillespie J W, Grover A, Tangrea M A, Chuaqui R F, Emmert-Buck M R, et al. Gene promoter methylation in prostate tumor-associated stromal cells. J Natl Cancer Inst. 2006; 98:255-61.

[3] Mehrotra J, Varde S, Wang H, Chiu H, Vargo J, Gray K, et al. Quantitative, spatial resolution of the epigenetic field effect in prostate cancer. Prostate. 2008; 68:152-60.

[4] Dakubo G D, Jakupciak J P, Birch-Machin M A, Parr R L. Clinical implications and utility of field cancerization. Cancer Cell Int. 2007; 7:2.

[5] Damaschke N A, Yang B, Bhusari S, Svaren J P, Jarrard D F. Epigenetic susceptibility factors for prostate cancer with aging. Prostate. 2013; 73:1721-30.

[6] Fu V X, Dobosy J R, Desotelle J A, Almassi N, Ewald J A, Srinivasan R, et al. Aging and cancer-related loss of insulin-like growth factor 2 imprinting in the mouse and human prostate. Cancer Res. 2008; 68:6797-802.

[7] Yang B, Bhusari S, Kueck J, Weeratunga P, Wagner J, Leverson G, et al. Methylation profiling defines an extensive field defect in histologically normal prostate tissues associated with prostate cancer. Neoplasia. 2013; 15:399-408.

[8] Truong M, Yang B, Livermore A, Wagner J, Weeratunga P, Huang W, et al. Using the epigenetic field defect to detect prostate cancer in biopsy negative patients. J Urol. 2013; 189:2335-41.

[9] Zhou M. High-grade prostatic intraepithelial neoplasia, PIN-like carcinoma, ductal carcinoma, and intraductal carcinoma of the prostate. Mod Pathol. 2018; 31:S71-9.

[10] Girasole C R, Cookson M S, Putzi M J, Chang S S, Smith J A, Wells N, et al. Significance of atypical and suspicious small acinar proliferations, and high grade prostatic intraepithelial neoplasia on prostate biopsy: implications for cancer detection and biopsy strategy. J Urol. 2006; 175:929-33; discussion 33.

[11] Page D L, Dupont W D. Anatomic markers of human premalignancy and risk of breast cancer. Cancer. 1990; 66:1326-35.

[12] McNeal J E. Normal histology of the prostate. Am J Surg Pathol. 1988; 12:619-33.

[13] Sandhu R, Chollet-Hinton L, Kirk E L, Midkiff B, Troester M A. Digital histologic analysis reveals morphometric patterns of age-related involution in breast epithelium and stroma. Hum Pathol. 2016; 48:60-8.

[14] Madabhushi A, Lee G. Image analysis and machine learning in digital pathology: Challenges and opportunities. Med Image Anal. 2016; 33:170-5.

[15] Tambasco M, Costello B M, Kouznetsov A, Yau A, Magliocco A M. Quantifying the architectural complexity of microscopic images of histology specimens. Micron. 2009; 40:486-94.

[16] Veltri R W, Park J, Miller M C, Marks L, Kojima M, van Rootselaar C, et al. Stromal-epithelial measurements of prostate cancer in native Japanese and Japanese-American men. Prostate Cancer Prostatic Dis. 2004; 7:232-7.

[17] Huang W, Hennrick K, Drew S. A colorful future of quantitative pathology: validation of Vectra technology using chromogenic multiplexed immunohistochemistry and prostate tissue microarrays. Hum Pathol. 2013; 44:29-38.

[18] Esbona K, Inman D, Saha S, Jeffery J, Schedin P, Wilke L, et al. COX-2 modulates mammary tumor progression in response to collagen density. Breast Cancer Res. 2016; 18:35.

[19] McGarry S D, Hurrell S L, Iczkowski K A, Hall W, Kaczmarowski A L, Banerjee A, et al. Radio-pathomic Maps of Epithelium and Lumen Density Predict the Location of High-Grade Prostate Cancer. Int J Radiat Oncol Biol Phys. 2018; 101:1179-87.

[20] Gore J L, Shariat S F, Miles B J, Kadmon D, Jiang N, Wheeler™, et al. Optimal combinations of systematic sextant and laterally directed biopsies for the detection of prostate cancer. J Urol. 2001; 165:1554-9.

[21] Yang B, Etheridge T, McCormick J, Schultz A, Khemees T A, Damaschke N, et al. Validation of an epigenetic field of susceptibility to detect significant prostate cancer from non-tumor biopsies. Clin Epigenetics. 2019; 11:168.

[22] Ghosh K, Vachon C M, Pankratz V S, Vierkant R A, Anderson S S, Brandt K R, et al. Independent association of lobular involution and mammographic breast density with breast cancer risk. J Natl Cancer Inst. 2010; 102:1716-23.

[23] Tambasco M, Magliocco A M. Relationship between tumor grade and computed architectural complexity in breast cancer specimens. Hum Pathol. 2008; 39:740-6.

[24] Chung L W. Implications of stromal-epithelial interaction in human prostate cancer growth, progression and differentiation. Semin Cancer Biol. 1993; 4:183-92.

[25] Hayward S W, Rosen M A, Cunha G R. Stromal-epithelial interactions in the normal and neoplastic prostate. Br J Urol. 1997; 79 Suppl 2:18-26.

[26] Lee M C, Moussa A S, Yu C, Kattan M W, Magi-Galluzzi C, Jones J S. Multifocal high grade prostatic intraepithelial neoplasia is a risk factor for subsequent prostate cancer. J Urol. 2010; 184:1958-62.

[27] McNeal J E, Redwine E A, Freiha F S, Stamey T A. Zonal distribution of prostatic adenocarcinoma. Correlation with histologic pattern and direction of spread. Am J Surg Pathol. 1988; 12:897-906.

[28] Iremashvili V, Pelaez L, Jorda M, Manoharan M, Arianayagam M, Rosenberg D L, et al. Prostate sampling by 12-core biopsy: comparison of the biopsy results with tumor location in prostatectomy specimens. Urology. 2012; 79:37-42.

[29] Howlader N, Noone A, Krapcho M, Miller D, Bishop K, Kosary C, et al. SEER Cancer Statistics Review, 1975-2014, based on November 2016 SEER data submission. National Cancer Institute, Bethesda, Md.; April 2017.

We claim:

1. A method of detecting and optionally treating prostate cancer in a human subject, the method comprising:
   obtaining histologically normal prostate tissue from the subject; and
   quantifying, comprising one or more of:
      quantifying an increase in epithelial thickness in the tissue of at least 6% relative to the epithelial thickness measured in a sample from a healthy, prostate tumor-free subject; and
      quantifying a decrease in gland lumen roundness in the tissue of at least 10% relative to the gland lumen roundness measured in a sample from a healthy, prostate tumor-free subject; and then
   performing a prostate cancer detection procedure on the subject.

2. The method of claim 1, comprising quantifying an increase in epithelial thickness in the tissue of at least 6% relative to the epithelial thickness measured in a sample from a healthy, prostate tumor-free subject.

3. The method of claim 1, comprising quantifying an increase in epithelial thickness in the tissue of at least 7% relative to the epithelial thickness measured in a sample from a healthy, prostate tumor-free subject.

4. The method of claim 1, comprising quantifying an increase in epithelial thickness in the tissue of at least 8% relative to the epithelial thickness measured in a sample from a healthy, prostate tumor-free subject.

5. The method of claim 1, comprising quantifying a decrease in gland lumen roundness in the tissue of at least 10% relative to the gland lumen roundness measured in a sample from a healthy, prostate tumor-free subject.

6. The method of claim 1, comprising quantifying a decrease in gland lumen roundness in the tissue of at least 12% relative to the gland lumen roundness measured in a sample from a healthy, prostate tumor-free subject.

7. The method of claim 1, comprising quantifying a decrease in gland lumen roundness in the tissue of at least 13% relative to the gland lumen roundness measured in a sample from a healthy, prostate tumor-free subject.

8. The method of claim 1, comprising:
   quantifying an increase in epithelial thickness in the tissue of at least 6% relative to the epithelial thickness measured in a sample from a healthy, prostate tumor-free subject; and
   quantifying a decrease in gland lumen roundness in the tissue of at least 10% relative to the gland lumen roundness measured in a sample from a healthy, prostate tumor-free subject.

9. The method of claim 1, wherein the prostate cancer detection procedure comprises a procedure selected from the group consisting of prostate tissue biopsy, imaging with an endorectal probe, and magnetic resonance imaging.

10. The method of claim 1, wherein the prostate cancer detection procedure comprises prostate tissue biopsy and at least one of imaging with an endorectal probe and magnetic resonance imaging.

11. The method of claim 1, wherein the prostate cancer detection procedure comprises prostate tissue biopsy.

12. The method of claim 1, wherein the prostate cancer detection procedure comprises prostate tissue biopsy performed with anesthesia.

13. The method of claim 1, wherein the prostate cancer detection procedure comprises prostate tissue biopsy, wherein the prostate tissue biopsy comprises removing at least 10 tissue cores from the subject.

14. The method of claim 1, wherein the prostate cancer detection procedure comprises prostate tissue biopsy, wherein the prostate tissue biopsy comprises removing at least 30 tissue cores from the subject.

15. The method of claim 1, further comprising, after the performing a prostate cancer detection procedure on the subject, treating the subject for prostate cancer.

* * * * *